US010154981B2

(12) United States Patent
Duval et al.

(10) Patent No.: US 10,154,981 B2
(45) Date of Patent: *Dec. 18, 2018

(54) USE OF A FEED COMPOSITION FOR REDUCING METHANE EMISSION IN RUMINANTS, AND/OR TO IMPROVE RUMINANT PERFORMANCE

(75) Inventors: Stephane Duval, Saint-Louis (FR); Irmgard Immig, Basel (CH); Maik Kindermann, Basel (CH); Gilbert Weber, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 344 days.

This patent is subject to a terminal disclaimer.

(21) Appl. No.: 14/119,990

(22) PCT Filed: May 25, 2012

(86) PCT No.: PCT/EP2012/059826
§ 371 (c)(1),
(2), (4) Date: Nov. 25, 2013

(87) PCT Pub. No.: WO2012/160191
PCT Pub. Date: Nov. 29, 2012

(65) Prior Publication Data
US 2014/0088161 A1    Mar. 27, 2014

(30) Foreign Application Priority Data

May 26, 2011    (EP) .................................... 11167748

(51) Int. Cl.
| | |
|---|---|
| A23K 50/30 | (2016.01) |
| A23K 20/163 | (2016.01) |
| A23K 20/10 | (2016.01) |
| A61K 31/21 | (2006.01) |
| A61K 31/221 | (2006.01) |
| A61K 31/24 | (2006.01) |
| A61K 31/255 | (2006.01) |
| A61K 31/275 | (2006.01) |
| A61K 31/34 | (2006.01) |
| A61K 31/351 | (2006.01) |
| A61K 31/4406 | (2006.01) |
| A61K 31/04 | (2006.01) |
| A61K 31/44 | (2006.01) |
| A23K 20/105 | (2016.01) |
| A23K 20/195 | (2016.01) |
| A23K 50/10 | (2016.01) |
| A61K 9/00 | (2006.01) |
| A61K 31/215 | (2006.01) |
| A61K 31/22 | (2006.01) |
| A61K 31/23 | (2006.01) |
| A61K 31/235 | (2006.01) |
| A61K 31/35 | (2006.01) |
| A61K 45/06 | (2006.01) |

(52) U.S. Cl.
CPC .............. *A61K 31/21* (2013.01); *A23K 20/10* (2016.05); *A23K 20/105* (2016.05); *A23K 20/195* (2016.05); *A23K 50/10* (2016.05); *A61K 9/0053* (2013.01); *A61K 31/04* (2013.01); *A61K 31/215* (2013.01); *A61K 31/22* (2013.01); *A61K 31/221* (2013.01); *A61K 31/23* (2013.01); *A61K 31/235* (2013.01); *A61K 31/24* (2013.01); *A61K 31/255* (2013.01); *A61K 31/275* (2013.01); *A61K 31/34* (2013.01); *A61K 31/35* (2013.01); *A61K 31/351* (2013.01); *A61K 31/44* (2013.01); *A61K 31/4406* (2013.01); *A61K 45/06* (2013.01); *Y02P 60/56* (2015.11)

(58) Field of Classification Search
CPC ...... A23K 50/30; A23K 20/10; A23K 20/163; A23K 1/16
See application file for complete search history.

(56) References Cited

U.S. PATENT DOCUMENTS

| | | | |
|---|---|---|---|
| 6,743,440 B1 | 6/2004 | Ballinger, Jr. | |
| 9,266,814 B2 | 2/2016 | Duval et al. | |
| 9,365,489 B2 * | 6/2016 | Duval | A61K 31/21 |

FOREIGN PATENT DOCUMENTS

| | | |
|---|---|---|
| EP | 0685169 | 12/1995 |
| EP | 1 727 787 | 12/2006 |
| GB | 1268952 | 3/1972 |
| JP | 2003-529333 | 7/2003 |
| WO | 01/26482 | 4/2001 |
| WO | 2009/098113 | 8/2009 |
| WO | 2010/072584 | 7/2010 |
| WO | WO 2010/072584 * | 7/2010 |
| WO | 2011/010921 | 1/2011 |
| WO | 2011/045418 | 4/2011 |

(Continued)

OTHER PUBLICATIONS

Bertinaria et al. (Drug Development Research 60:225-239 (2003)).*
Fagerholm et al, "Pre-clinical pharmacokinetics of the cyclooxygenase-inhibiting nitric oxide donor (CINOD) AZD3582," Journal of Pharmacy and Pharmacology, JPP 2005, 57: 587-597.
International Search Report for PCT/EP2012/059826, dated Dec. 12, 2012.
Anderson, R.C. et al., "Effects of select nitrocompounds on in vitro ruminal fermentation during conditions of limiting or excess added reductant", Bioresource Technology, vol. 99, No. 18, (Dec. 1, 2008), pp. 8655-8661.

(Continued)

*Primary Examiner* — Jeffrey S Lundgren
*Assistant Examiner* — Chris E Simmons
(74) *Attorney, Agent, or Firm* — Nixon & Vanderhye P.C.

(57) ABSTRACT

The present invention relates to the field of reduction of methane emission in ruminants. Particularly, it relates to the use of a feed composition or a feed additive comprising at least one antibiotic and at least one organic molecule substituted at any position with at least one nitrooxy group for reducing the production of methane emanating from the digestive activities of ruminants, and/or to improve the ruminant performance.

15 Claims, No Drawings

(56) References Cited

FOREIGN PATENT DOCUMENTS

WO    WO/2011/070133    *   6/2011

OTHER PUBLICATIONS

Busquet, M et al., "Effect of garlic oil and four of its compounds on rumen microbial fermentation", Journal of Dairy Science, vol. 88, (Jan. 1, 2005), pp. 4393-4404.
Anderson, Robin C., "*Effects of select nitrocompounds on in vitro ruminal fermentation during conditions of limiting or excess added reductant*", Bioresource Technology, Elsevier B.V., 2008, vol. 99, Issue 18, pp. 8655-8661.
Fagerholm, "*Pre-Clinical Pharmacokinetics of the Cyclooxygenase-Inhibiting Nitric Oxide Donor(cinod) AZD3582*", J.Pharmacy and Pharmacology, May 1, 2005, V57 N5, pp. 587-597.

* cited by examiner

USE OF A FEED COMPOSITION FOR REDUCING METHANE EMISSION IN RUMINANTS, AND/OR TO IMPROVE RUMINANT PERFORMANCE

This application is the U.S. national phase of International Application No. PCT/EP2012/059826, filed 25 May 2012, which designated the U.S. and claims priority to EP Application No. 11167748.0, filed 26 May 2011, the entire contents of each of which are hereby incorporated by reference.

The present invention relates to the field of reduction of methane emission in ruminants. Particularly, it relates to the use of a feed composition or a feed additive comprising at least one antibiotic and at least one organic molecule substituted at any position with at least one nitrooxy group, for reducing the production of methane emanating from the digestive activities of ruminants, and/or to improve the ruminant performance.

The present invention further relates to animal feed or animal feed compositions and feed additives comprising the above mentioned molecules. The term feed or feed composition means any compound, preparation, mixture, or composition suitable for, or intended for intake by an animal.

In the present context, a ruminant is a mammal of the order Artiodactyla that digests plant-based food by initially softening it within the animal's first stomach, known as the rumen, then regurgitating the semi-digested mass, now known as cud, and chewing it again. The process of again chewing the cud to further break down plant matter and stimulate digestion is called "ruminating".

Rumen fermentation brings some disadvantages. Methane is produced as a natural consequence of the anaerobic fermentation, which represents an energy loss to the host animal. Carbohydrate makes up 70 to 80% of the dry matter in a typical dairy cattle ration and in spite of this the absorption of carbohydrates from the gastro-intestinal tract is normally very limited. The reason for this is the extensive fermentation of carbohydrates in the rumen resulting in production of acetate, propionate and butyrate as the main products. These products are part of the so called volatile fatty acids, (VFAs).

Besides the energy loss, methane is also a greenhouse gas, which is many times more potent than $CO_2$. Its concentration in the atmosphere has doubled over the last century and continues to increase alarmingly. Ruminants are the major contributors to the biogenic methane formation, and it has been estimated that the prevention of methane formation from ruminants would almost stabilize atmospheric methane concentrations.

Furthermore, the assessment of the Kyoto protocol followed by the Copenhagen climate summit in 2009 places increased priority in decreasing methane emissions as part of a multi-gas strategy.

Antibiotics and more particularly ionophores have been shown to slightly reduce methane production in ruminants (Guan et al. 2006. Journal of Animal Science; 84: 1896-1906). However, the effect of antibiotics on the formation of methane has some disadvantages because of rapid adaptation of the microflora and/or resistance development leading to a complete loss of the intended effect within a short period of time (2 to 3 weeks), and because the use of antibiotics is banned in Europe for non therapeutic use.

Non antibiotic products (bile acid derivatives) leading to reduction of methane emission, when tested using an in vitro rumen simulation model, have recently been published (WO 2010/072584). However, the amount required to produce a moderate reduction of methane emission are not compatible with the ruminant feed industry cost constraints.

Furthermore, a number of natural plant extracts (Garlic: WO 2009/150264, yucca, cinnamon, rhubarb . . . ) have been described in the scientific literature as potent solutions to reduce methane emission in ruminants based on in vitro experiments. However, none of these solutions made it to a commercial product because of side effects (residues in milk), because of lack efficacy, when tested in vivo, or because of the very large amount of additive which needs to be supplied to the animal to generate a significant methane reduction.

Under these circumstances there is still a need to develop new substances and compositions which reduce the formation of methane produced by ruminants. In addition to reducing methane emission, such compositions may also contribute to improve ruminant performance by improving the feed conversion ratio, reducing feed intake, improving weight gain, and/or improving carcass, or milk yield.

The present inventors now surprisingly found that the composition specified herein after, have a great potential for use in animal feed in order to essentially reduce the formation of methane without affecting microbial fermentation in a way that would be detrimental to the host animal. Moreover, the compounds of the present invention also have a great benefit regarding overall animal performance as measured by ruminal acetate/propionate ratio, feed conversion ratio, feed intake, weight gain, carcass yield, or milk yield. Said compositions are also more stable than those described in the prior art, safer for the animal and human, lead to persistent methane reduction effect, they do not affect palatability, they can be produced at industrial scale at a cost compatible with the animal nutrition industry, and above all, they do not provoke accumulation of any metabolite in the milk or meat of the supplemented animal, and they are active at very low concentration in the rumen.

Therefore, the present invention provides the use of a feed composition or feed additive comprising at least one antibiotic, and at least one organic molecule substituted at any position with at least one nitrooxy group, or a salt thereof as defined by formula (I) for reducing the formation of methane emanating from the digestive activities of ruminants and/or for improving ruminant performance.

The invention further provides a method for reducing the production of methane emanating from the digestive activities of ruminants and/or for improving ruminant animal performance, comprising orally administering to the animal a sufficient amount of a feed composition or feed additive comprising at least one antibiotic, and at least one organic molecule substituted at any position with at least one nitrooxy group, or a salt thereof as defined by formula (I) to the animal. It is to be understood by oral administration, a simple feeding, or manual administration of a bolus.

In all embodiments of the present invention, organic molecules substituted at any position with at least one nitrooxy group, or salts thereof are defined by the following formula (I):

formula (I)

wherein Y is an organic molecule of the following composition: $C_aH_bO_dN_eS_g$, wherein
a is comprised between 1 and 25, preferably between 1 and 10
b is comprised between 2 and 51, preferably between 2 and 21
d is comprised between 0 and 8, preferably between 0 and 6
e is comprised between 0 and 5, preferably between 0 and 3
g is comprised between 0 and 3, preferably between 0 and 1.

More preferably, in all embodiments of the present invention, the organic molecule of formula (I) is of the following composition $C_aH_bO_dN_eS_g$, wherein
a is comprised between 1 and 10
b is comprised between 2 and 21
d is comprised between 0 and 6
e is comprised between 0 and 3
g is comprised between 0 and 1, In another embodiment, preferred compounds of formula (I) according to the present invention are compounds, wherein b is comprised between 3 and 51, preferably, b is comprised between 3 and 21.

In another embodiment, preferred compounds of formula (I) according to the present invention are compounds of formula (II),

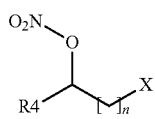

formula (II)

wherein
n is comprised between 0 and 12, preferably comprised between 0 and 6 and, wherein, if n≠0, the carbon chain is a linear, a cyclic, or branched aliphatic carbon chain which may be non substituted or substituted with up to 3 hydroxyl-, alkoxy-, amino-, alkylamino-, dialkylamino- or nitrooxy groups, or an alkenyl, or an alkynyl carbon chain mono- or polyunsaturated and in any isomeric form, R4 is independently, hydrogen or a saturated straight, cyclic or branched chain of an alkyl or alkenyl group containing 1 to 12, preferably 1 to 6 carbon atoms,
X is hydrogen, R5, R5≡N, —OR5, —OCOR5, —NR5R6, —ONO2, —COOR5, —CONR5R6, —NHSO2R5, or —SO2NHR5,
R5 and R6 are independently, hydrogen, C1-C12 straight, branched or cyclic alkyl chain, non substituted or substituted with up to 3 hydroxyl-, alkoxy-, amino-, alkylamino-, dialkylamino- or nitrooxy groups, alkenyl, or alkynyl carbon chain which may be mono or polyunsaturated, and in any isomeric form.

For all embodiments of the present invention, it is to be understood that compounds of formula (I) and compounds of formula (II) can be in any isomeric form.

It is to be understood in the above definition of compounds of formula (II) that when n>2, the carbon chain can be linear or branched at any position along the carbon chain. In addition, the carbon chain can be branched by multiple branches at different positions along the carbon chain. Moreover, when n>3, the aliphatic carbon chain may form a cyclic moiety. This cyclic moiety can carry the nitrooxy moiety at any position (2, 3, 4), and it can also be branched at multiple positions by any aliphatic groups. The branched aliphatic groups are preferably, methyl, ethyl or propyl. Moreover, the carbon chain may be further substituted with up to 3 hydroxyl-, alkoxy-, amino-, alkylamino-, dialkylamino- or nitrooxy groups.

In the above definition of derivatives of the formula (II) a preferred alkyl group is methyl, ethyl, propyl, isopropyl, butyl, sec. butyl, isobutyl, pentyl, neopentyl, hexyl, cyclohexyl, and 2-ethyl-hexyl and octyl. Furthermore any alkyl or alkenyl group containing three or more carbon atoms can be straight chain, branched, or cyclic. In addition for the straight chain or branched $C_2$-$C_{10}$-alkenylene group, this is understood to encompass alkenylene groups with one or (from $C_4$) more double bonds; examples of such alkenylene groups are those of the formulae —CH═CH—, —CH═CH—CH2—, —CH═CH—(CH2)3— and —(CH═CH)2—.

In another embodiment, more preferred compounds of formula (I) according to the present invention are selected from the list of compounds, and salts thereof as listed with their chemical formula in Table 1.

TABLE 1

| Preferred compounds of formula (I) according to the present invention | | |
|---|---|---|
| Comp. Identifier | Molecular structure | Chemical name |
| 1 | HO⁀⁀⁀O⁀NO2 | 3-Nitrooxypropanol |
| 2 | (phenyl-CH2-CH2-CH(ONO2)-CH2-ONO2) | rac-4-Phenylbutane-1,2-diyl dinitrate |
| 3 | C(CH2ONO2)(CH2OH)(CH2OH)(CH2OH) | 2-(Hydroxymethyl)-2-(nitrooxymethyl)-1,3-propanediol |

TABLE 1-continued

Preferred compounds of formula (I) according to the present invention

| Comp. Identifier | Molecular structure | Chemical name |
|---|---|---|
| 4 | (structure) | N-Ethyl-3-nitro-oxy-propionic sulfonyl amide |
| 5 | (structure) | 5-Nitrooxy-pentanenitrile |
| 6 | (structure) | 5-Nitrooxy-pentane |
| 7 | (structure) | 3-Nitro-oxy-propyl propionate |
| 8 | (structure) | 1,3-bis-Nitrooxypropane |
| 9 | (structure) | 1,4-bis-Nitrooxybutane |
| 10 | (structure) | 1,5-bis-Nitrooxypentane |
| 11 | (structure) | 3-Nitro-oxy-propyl benzoate |
| 12 | (structure) | 3-Nitro-oxy-propyl hexanoate |
| 13 | (structure) | 3-Nitro-oxy-propyl 5-nitro-oxy-hexanoate |
| 14 | (structure) | Benzylnitrate |
| 15 | (structure) | isosorbid-dinitrate |
| 16 | (structure) | N-[2-(Nitrooxy)ethyl]-3-pyridinecarboxamide |
| 17 | (structure) | 3-nitrooxy propionic acid |
| 18 | (structure) | methyl-3-nitrooxy propionate |

TABLE 1-continued

Preferred compounds of formula (I) according to the present invention

| Comp. Identifier | Molecular structure | Chemical name |
|---|---|---|
| 19 | $O_2N\sim O\sim\sim C(O)O\sim$ | Ethyl-3-nitrooxy propionate |
| 20 | $O_2N\sim O\sim\sim\sim C(O)O\sim$ | Ethyl-4-nitrooxy butanoate |
| 21 | $O_2N\sim O\sim CH(CH_3)\sim C(O)O\sim$ | Ethyl-3-nitrooxy butanoate |
| 22 | $O_2N\sim O\sim\sim\sim\sim C(O)OH$ | 5-nitrooxy pentanoic acid |
| 23 | $O_2N\sim O\sim\sim\sim\sim C(O)O\sim$ | Ethyl-5-nitrooxy pentanoate |
| 24 | $O_2N\sim O\sim\sim\sim\sim\sim C(O)OH$ | 6-nitrooxy hexanoic acid |
| 25 | $O_2N\sim O\sim\sim\sim\sim\sim C(O)O\sim$ | Ethyl-6-nitrooxy hexanoate |
| 26 | $O_2N\sim O\text{-cyclohexyl-}C(O)O\sim$ | ethyl-4-nitrooxy-cyclohexylcarboxylate |
| 27 | $O_2N\sim O\sim\sim\sim\sim\sim\sim\sim C(O)OH$ | 8-nitrooxy octanoic acid |
| 28 | $O_2N\sim O\sim\sim\sim\sim\sim\sim\sim C(O)O\sim$ | Ethyl-8-nitrooxy octanoate |
| 29 | $O_2N\sim O\sim\sim\sim\sim\sim\sim\sim\sim\sim C(O)OH$ | 11-nitrooxy undecanoic acid |
| 30 | $O_2N\sim O\sim\sim\sim\sim\sim\sim\sim\sim\sim C(O)O\sim$ | Ethyl-11-nitrooxy undecanoate |
| 31 | $O_2N\sim O\sim\sim\sim\sim C(O)NH_2$ | 5-nitrooxy-pentanoic amide |
| 32 | $O_2N\sim O\sim\sim\sim\sim C(O)NHCH_3$ | 5-nitrooxy-N-methyl-pentanoic amide |

In another embodiment, even more preferred compounds of formula (I) are selected from the list of compounds, and salts thereof comprising 3-Nitrooxypropanol, ethyl-3-nitrooxy propionate, methyl-3-nitrooxy propionate, and 3-nitrooxy propionic acid.

The compounds of formula (I) the present invention also comprise salts of the nitrooxy organic molecule. Preferred cations for salt preparation may be selected from the group consisting of sodium (Na+), potassium (K+), lithium (Li+), magnesium (Mg2+), calcium (Ca2+), barium (Ba2+), strontium (Sr2+), and ammonium (NH4+). Salts may also be prepared from an alkali metal or an alkaline earth metal.

The compounds of formula (I) according to the present invention can be manufactured in principle according to synthetic methods known per se for nitrooxy organic molecules, and/or based on methods as described in PCT/EP2010/069338, and in the European patent application No. 10 195 857.7.

In all these cases appropriate methods to purify the product (compounds of formula (I)) can be chosen by those skilled in the art, i.e. by column chromatography, or the compound of formula (I), can be isolated and purified by methods known per se, e.g. by adding a solvent such as diethyl-ether or ethyl acetate to induce the separation of the crude product from the mixture after reaction, and drying over $Na_2SO_4$ of the collected crude product.

Antibiotics are substances that kill or slow down the growth of microorganisms. As a specific antibiotic class, ionophores are generally defined as substances that facilitate translocation of an ion across a lipid barrier such as a cell membrane.

In a particular embodiment of this invention, the at least one antibiotic is selected from the group consisting of monensin, lasalocid, narasin, maduramycin, semduramycin, salinomycin, avoparcin, actaplanin, and penicillin. More preferably, compounds most suited to this invention are ionophores, and even most preferably, the antibiotic is either monensin (Rumensin) or lasalocid (Bovatec). Both ionophores are available from Elanco and Alpharma respectively.

Methane emission by ruminants can easily be measured in individual animals in metabolic chambers by methods known in the art (Grainger et al., 2007 J. Dairy Science; 90: 2755-2766). Moreover, it can also be assessed at barn level by an emerging technology using laser beam (McGinn et al., 2009, Journal of Environmental Quality; 38: 1796-1802). Alternatively, methane produced by a dairy ruminant can also be assessed by measurement of fatty acid profiles in milk according to WO 2009/156453.

Ruminant performance can be assessed by methods well known in the art, and is usually characterized by feed conversion ratio, feed intake, weight gain, carcass yield, or milk yield.

The present invention also relates to the use of a feed composition or feed additive comprising at least one antibiotic, and at least one organic molecule substituted at any position with at least one nitrooxy group, or a salt thereof as defined by formula (I) in combination with at least one additional active substance which shows similar effects with regard to methane formation in the rumen and which is selected from the group consisting of diallyl disulfide, garlic oil, allyl isothiocyanate, deoxycholic acid, chenodeoxycholic acid and derivatives thereof.

Further components that could be given together with the compound according to the present invention are for example yeasts, oregano extracts, and essential oils e.g. thymol, 3-methylphenol, vaniline, guajacol and eugenol.

It is at present contemplated that diallyl disulfide, garlic oil, allyl isothiocyanate deoxycholic acid, chenodeoxycholic acid and derivatives thereof are independently administered in dosage ranges of for example 0.01-500 mg active substance per kg feed (ppm). These compounds are either commercially available or can easily be prepared by a skilled person using processes and methods well-known in the prior art.

Ruminating mammals according to the present invention include cattle, goats, sheep, giraffes, American Bison, European bison, yaks, water buffalo, deer, camels, alpacas, llamas, wildebeest, antelope, pronghorn, and nilgai.

For all embodiments of the present invention, domestic cattle, sheep and goat are the more preferred species. For the present purposes most preferred species are domestic cattle. The term includes all races of domestic cattle, and all production kinds of cattle, in particular dairy cows and beef cattle.

The present invention also relates to the use of a feed composition or feed additive comprising at least one antibiotic, and at least one organic molecule substituted at any position with at least one nitrooxy group, or a salt thereof as defined by formula (I), wherein the methane production in ruminants calculated in liters per kilogram of dry matter intake is reduced by at least 10% when measured in metabolic chambers. Preferably, methane reduction is at least 15%, more preferably, at least 20%, even more preferably, at least 25%, most preferably, at least 30%. Alternative methane emission measurements may also be used like using a laser beam or for dairy ruminants, correlating methane production to the VFA profile in milk.

The present invention also relates to the use of a feed composition or feed additive comprising at least one antibiotic, and at least one organic molecule substituted at any position with at least one nitrooxy group, or a salt thereof as defined by formula (I), wherein the ruminant feed conversion ratio is reduced by at least 1% when measured in conventional performance trial. Preferably, the feed conversion ratio is reduced by at least 2%, more preferably, by at least 2.5%, even more preferably, by at least 3%, most preferably, by at least 3.5%.

In animal husbandry, the term feed conversion ratio (FCR), is a measure of an animal's efficiency in converting feed mass into increased body mass. Specifically FCR is the mass of the feed eaten divided by the body mass gain, all over a specified period of time. FCR is dimensionless.

The present invention also relates to the use of a feed composition or feed additive comprising at least one antibiotic, and at least one organic molecule substituted at any position with at least one nitrooxy group, or a salt thereof as defined by formula (I), wherein the amount of the organic molecule as defined in formula (I) administered to the ruminant animal is from 1 mg to 10 g per Kg of feed, preferably from 10 mg to 1 g per Kg of feed, more preferably, from 50 mg to 500 mg per Kg of feed, and the amount of antibiotic administered to the ruminant animal is from 0.5 to 150 mg per Kg of feed, preferably from 0.5 to 100 mg per Kg of feed, and most preferably from 5 to 50 mg per Kg of feed. For the use in animal feed, however, organic molecules substituted at any position with at least one nitrooxy group, or their salts thereof as defined by formula (I) need not be that pure; it may e.g. include other compounds and derivatives.

The present invention further relates to the use of a feed composition or feed additive comprising at least one antibiotic, and at least one organic molecule substituted at any position with at least one nitrooxy group, or a salt thereof as defined by formula (I), wherein the weight ratio of organic molecule as defined in formula (I/antibiotic in the feed composition or feed additive is comprised between 0.05 and 50, preferably between 0.1 and 10, more preferably between 0.5 and 5.

Ruminant feed or feed additives may be prepared by methods known per se in the art of feed formulation and processing.

Further aspects of the present invention are therefore formulations, i.e. feed additives and animal feed compositions containing compositions as herein above defined.

The present invention therefore also relates to a feed composition or a feed additive comprising at least one antibiotic and at least a compound of formula (I) or a salt thereof. In a preferred embodiment, the composition is a mineral premix, a vitamin premix including vitamins and minerals or a bolus.

The normal daily dosage of a composition according to the invention provided to an animal by feed intake depends upon the kind of animal and its condition. Normally this dosage should be in the range of from about 1 mg to about 10 g, preferably from about 10 mg to about 1 g, more preferably, 50 mg to 500 mg compound per kg of feed.

The composition comprising at least one antibiotic and at least one organic molecule substituted at any position with at least one nitrooxy group, or a salt thereof as defined by formula (I) may be used in combination with conventional ingredients present in an animal feed composition (diet) such as calcium carbonates, electrolytes such as ammonium chloride, proteins such as soya bean meal, wheat, starch, sunflower meal, corn, meat and bone meal, amino acids, animal fat, vitamins and trace minerals.

Particular examples of compositions of the invention are the following:

An animal feed additive comprising (a) at least one compound selected from table 1 and (b) an antibiotic, (c) at least one fat-soluble vitamin, (d) at least one water-soluble vitamin, (e) at least one trace mineral, and/or (f) at least one macro mineral;

An animal feed composition comprising an antibiotic and at least one compound selected from table 1 and a crude protein content of 50 to 800 g/kg feed.

The so-called premixes are examples of animal feed additives of the invention. A premix designates a preferably uniform mixture of one or more micro-ingredients with diluents and/or carrier. Premixes are used to facilitate uniform dispersion of micro-ingredients in a larger mix.

Apart from the active ingredients of the invention, the premix of the invention contains at least one fat-soluble vitamin, and/or at least one water soluble vitamin, and/or at least one trace mineral, and/or at least one macro mineral. In other words, the premix of the invention comprises the at least one compound according to the invention together with at least one additional component selected from the group consisting of fat-soluble vitamins, water-soluble vitamins, trace minerals, and macro minerals.

Macro minerals may be separately added to the feed. Therefore, in a particular embodiment, the premix comprises the active ingredients of the invention together with at least one additional component selected from the group consisting of fat-soluble vitamins, water-soluble vitamins, and trace-minerals.

The following are non-exclusive lists of examples of these components:

Examples of fat-soluble vitamins are vitamin A, vitamin D3, vitamin E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

As regards feed compositions for ruminants such as cows, as well as ingredients thereof, the ruminant diet is usually composed of an easily degradable fraction (named concentrate) and a fiber-rich less readily degradable fraction (named hay, forage, or roughage).

Hay is made of dried grass, legume or whole cereals. Grasses include among others timothy, ryegrasses, fescues. Legumes include among others clover, lucerne or alfalfa, peas, beans and vetches. Whole cereals include among others barley, maize (corn), oat, sorghum. Other forage crops include sugarcane, kales, rapes, and cabbages. Also root crops such as turnips, swedes, mangles, fodder beet, and sugar beet (including sugar beet pulp and beet molasses) are used to feed ruminants. Still further crops are tubers such as potatoes, cassava and sweet potato. Silage is an ensiled version of the fiber-rich fraction (e.g. from grasses, legumes or whole cereals) whereby material with a high water content is treated with a controlled anaerobic fermentation process (naturally-fermented or additive treated).

Concentrate is largely made up of cereals (such as barley including brewers grain and distillers grain, maize, wheat, sorghum), but also often contain protein-rich feed ingredients such as soybean, rapeseed, palm kernel, cotton seed and sunflower.

Cows may also be fed total mixed rations (TMR), where all the dietary components, e.g. forage, silage and concentrate, are mixed before serving.

As mentioned above a premix is an example of a feed additive which may comprise the active compounds according to the invention. It is understood that the compounds may be administered to the animal in different other forms. For example the compounds can also be included in a bolus that would be placed in the rumen and that would release a defined amount of the active compounds continuously in well defined dosages over a specific period of time.

The present invention further relates to a method for reducing the production of methane emanating from the digestive activities of ruminants and/or for improving ruminant animal performance, comprising orally administering a sufficient amount of a feed composition or feed additive comprising at least one antibiotic, and at least one organic molecule substituted at any position with at least one nitrooxy group, or a salt thereof as defined by formula (I) with the preferred embodiments described above.

Moreover, the invention further relates to a method as described above, wherein the feed composition or feed additive according to the present invention is administered to the animal in combination with at least one additional active substance selected from the group consisting of diallyl disulfide, garlic oil, allyl isothiocyanate, deoxycholic acid, chenodeoxycholic acid and derivatives thereof.

The invention also relates to a method as described above, wherein the ruminant animal is selected from the group consisting of: cattle, goats, sheep, giraffes, American Bison, European bison, yaks, water buffalo, deer, camels, alpacas, llamas, wildebeest, antelope, pronghorn, and nilgai, and more preferably from the group consisting of: cattle, goats and sheep.

The invention also relates to a method as described above, wherein the amount of the at least one organic molecule as defined in formula (I) administered to the ruminant animal is from about 1 mg to about 10 g per kg feed, preferably from about 10 mg to about 1 g, more preferably from 50 mg to 500 mg compound per kg of feed, and the amount of antibiotic administered to the ruminant animal is from 0.5 to 150 mg per Kg of feed, preferably from 5 to 50 mg per Kg of feed.

The invention also relates to a method as described above, wherein the methane production in ruminants calculated in liters per kilogram of dry matter intake is reduced by at least 10% when measured in metabolic chambers. Preferably, methane reduction is at least 15%, more preferably, at least 20%, even more preferably, at least 25%, most preferably, at least 30%. Alternative methane emission measurements may also be used like using a laser beam or for dairy ruminants, correlating methane production to the VFA profile in milk.

The invention also relates to a method as described above, wherein the ruminant feed conversion ratio is reduced by at least 1% when measured in conventional performance trial. Preferably, the feed conversion ratio is reduced by at least 2% more preferably, by at least 2.5%, even more preferably, by at least 3%, most preferably, by at least 3.5%.

The invention also relates to a method as described above, wherein the weight ratio of organic molecule as defined in formula (I/antibiotic in the feed composition or feed additive is comprised between 0.05 and 50, preferably between 0.1 and 10, more preferably between 0.5 and 5.

The present invention is further described by the following examples which should not be construed as limiting the scope of the invention.

EXAMPLES

Example 1: In Vitro Test for Methane Production

A modified version of the "Hohenheim Forage value Test (HFT)" was used for testing the effect of specific compounds on the rumen functions mimicked by this in-vitro system.

Principle:

Feed is gadded into a syringe with a composition of rumen liquor and an appropriate mixture of buffers. The solution is incubated at 39° C. After 8 hours the quantity (and composition) of gas phase produced is measured and put into a formula for conversion.

Reagents:

Mass Element Solution:
6.2 g potassium dihydrogen phosphate ($KH_2PO_4$)
0.6 g magnesium sulfate heptahydrate ($MgSO_4*7H_2O$)
9 ml concentrated phosphoric acid (1 mol/l)
dissolved in distilled water to 1 l (pH about 1.6)

Buffer Solution:
35.0 g sodium hydrogen carbonate ($NaHCO_3$)
4.0 g ammonium hydrogen carbonate (($NH_4$)$HCO_3$) dissolved in distilled water to 1 l Trace Element Solution:
13.2 g calcium chloride dihydrate ($CaCl_2*2H_2O$) 10.0 g manganese(II) chloride tetrahydrate ($MnCl_2*4H_2O$)
1.0 g cobalt(II) chloride hexahydrate ($CoCl_2*6H_2O$)
8.0 g iron(III) chloride ($FeCl_3*6H_2O$)
dissolved in distilled water to 100 ml Sodium Salt Solution:
100 mg sodium salt
dissolved in distilled water to 100 ml Reduction Solution:
first 3 ml sodium hydroxide (c=1 mol/l), then 427.5 mg sodium sulfide hydrate ($Na_2S*H_2O$) are added to 71.25 ml $H_2O$ solution must be prepared shortly before it is added to the medium solution Procedure:

Sample Weighing:

The feed stuff is sieved to 1 mm—usually TMR (44% concentrate, 6% hay, 37% maize silage and 13% grass silage)—and weighed exactly into 64 syringes. 4 of these syringes are the substrate controls, which display the gas production without the effect of the tested compounds. 4 other syringes are positive control, in which bromoethane sulfonate has been added to 0.1 mM. When needed, 4 syringes contain a carrier control (if the test compounds need a carrier). The remaining syringes contain the test substances, by groups of 4 syringes.

Preparation of the Medium Solution:

The components are mixed in a Woulff bottle in following order:

711 ml water 0.18 ml trace element solution 355.5 ml buffer solution 355.5 ml mass element solution The completed solution is warmed up to 39° C. followed by the addition of 1.83 ml sodium salt solution and the addition of reduction solution at 36° C.

The rumen liquor is added, when the indicator turns colourless.

Extraction of the Rumen Liquor:

750 ml of rumen liquor are added to approximately 1,400 ml of medium solution under continued agitation and $CO_2$-gassing.

Filling the Syringes, Incubation and Determining Gas Volumes and VFA Values:

The diluted rumen fluid (24 ml) is added to the glass syringe. The syringes are then incubated for 8 hours at 39° C. under gentle agitation. After 8 hours, the volume of gas produced is measured, and the percentage of methane in the gas phase is determined by gas chromatography.

Results

The food fermented was artificial TMR (44% concentrate, 6% hay, 37% maize silage and 13% grass silage). Monensin was obtained from Elanco, and used at a concentration of 0.01% dry matter (DM). 3-nitrooxy-pentanol was used at two different concentrations 0.01% and 0.005% DM.

The results are presented in the following Table 2. Clear additive effects were obtained. Surprisingly, even with maximal methane inhibition when 3-nitrooxy propanol was used at 0.01% DM, further additive effect was observed on the acetate/propionate ratio when combined with monensin, which translates into additional performance benefit for the animal.

TABLE 2

Effect on Methane reduction, volatile fatty acids (VFA) production and VFA profile resulting from the average of three experiments with either monensin, 3-nitrooxy propanol, or combination of both. Ace. = acetate; Prop. = propionate; But = butyrate.

| Composition | Dose (% DM) | Effect on Methanogenesis (% compared to control) | Effect on VFA production (% compared to control) | VFA profile (as percentage of total VFA) | | |
|---|---|---|---|---|---|---|
| | | | | Ace. | Prop. | But. |
| Monensin | 0.01 | −23% | −6% | 56 | 38 | 6 |
| 3-nitrooxy propanol | 0.01 | −97% | −13% | 50 | 42 | 8 |
| 3-nitrooxy propanol | 0.005 | −21% | −3% | 57 | 36 | 7 |
| 3-nitrooxy propanol + Monensin | 0.01 + 0.01 | −99% | −15% | 46 | 47 | 7 |
| 3-nitrooxy propanol + Monensin | 0.005 + 0.01 | −48% | −8% | 52 | 41 | 7 |
| Negative control | | | | 60 | 33 | 7 |

The invention claimed is:

1. A feed composition or feed additive for a ruminant animal comprising:
   (i) at least one antibiotic, and
   (ii) at least one organic molecule or a salt thereof which is selected from the group consisting of 3-nitrooxypropanol, rac-4-Phenylbutane-1,2-diyl dinitrate, 2-(hydroxymethyl)-2-(nitrooxymethyl)-1,3-propanediol, N-ethyl-3-nitro-oxy-propionic sulfonyl amide, 5-nitrooxy-pentanenitrile, 5-nitrooxy-pentane, 3-nitro-oxy-propyl propionate, 1,3-bis-nitrooxypropane, 1,4-bis-nitrooxybutane, 1,5-bis-nitrooxypentane, 3-nitro-oxy-propyl benzoate, 3-nitro-oxy-propyl hexanoate, 3-nitro-oxy-propyl 5-nitro-oxy-hexanoate, benzylnitrate, isosorbid-dinitrate, N-[2-(nitrooxy)ethyl]-3-pyridinecarboxamide, 3-nitrooxy propionic acid, methyl-3-nitrooxy propionate, ethyl-3-nitrooxy propionate, ethyl-4-nitrooxy butanoate, ethyl-3-nitrooxy butanoate, 5-nitrooxy pentanoic acid, ethyl-5-nitrooxy pentanoate, 6-nitrooxy hexanoic acid, ethyl-6-nitrooxy hexanoate, ethyl-4-nitrooxy-cyclohexylcarboxylate, 8-nitrooxy octanoic acid, ethyl-8-nitrooxy octanoate, 11-nitrooxy undecanoic acid, ethyl-11-nitrooxy undecanoate, 5-nitrooxy-pentanoic amide and 5-nitrooxy-N-methyl-pentanoic amide, wherein
   the at least one organic molecule is present in an amount sufficient to reduce formation of methane emanating from digestive activities of the ruminant animal and/or to improve performance of the ruminant animal, and wherein
   the at least one organic molecule and the at least one antibiotic are present in a weight ratio of the at least one organic molecule to the at least one antibiotic of between 0.05 and 50.

2. The feed composition or feed additive of claim 1 which is a form selected from the group consisting of a mineral premix, a vitamin premix, premix including vitamins and minerals, and a bolus.

3. The feed composition or feed additive of claim 1, wherein the antibiotic is at least one selected from the group consisting of monensin, lasalocid, narasin, maduramycin, semduramycin, salinomycin, avoparcin, actaplanin, and penicillin.

4. The feed composition or feed additive of claim 1, which further comprises at least one additional active substance selected from the group consisting of diallyl disulfide, garlic oil, allyl isothiocyanate, deoxycholic acid, chenodeoxycholic acid and derivatives thereof.

5. The feed composition or feed additive of claim 1, wherein the ruminant animal is selected from the group consisting of cattle, goats, sheep, giraffes, American Bison, European bison, yaks, water buffalo, deer, camels, alpacas, llamas, wildebeest, antelope, pronghorn, and nilgai.

6. The feed composition or feed additive of claim 1, wherein the organic molecule is present in an amount sufficient to reduce formation of methane emanating from digestive activities of ruminants calculated in liters per kilogram of dry matter intake by at least 10% when measured in metabolic chambers.

7. The feed composition or feed additive of claim 1, wherein the amount of the at least one organic molecule is present in an amount of 1 mg to 10 g per kg feed.

8. The feed composition or feed additive of claim 1, wherein the amount of the at least one antibiotic is present in an amount from 0.5 to 150 mg per kg feed.

9. A feed composition or feed additive for a ruminant animal comprising:
   (i) at least one antibiotic, and
   (ii) at least one nitrooxy compound or salt thereof selected from the group consisting of 3-nitrooxy propanol, ethyl-3-nitrooxy propionate, methyl-3-nitrooxy propionate, and 3-nitrooxy propionic acid in an amount sufficient to reduce formation of methane emanating from digestive activities of the ruminant animal calculated in liters per kilogram of dry matter intake by at least 10% when measured in metabolic chambers.

10. The feed composition or feed additive as in claim 9, wherein the at least one nitrooxy compound is 3-nitrooxy propanol which is present in an amount from 1 mg to 10 g per kg feed.

11. The feed composition or feed additive of claim 10, wherein the amount of the at least one antibiotic is present in an amount from 0.5 to 150 mg per kg feed.

12. The feed composition or feed additive of claim 9 which is a form selected from the group consisting of a mineral premix, a vitamin premix, premix including vitamins and minerals, and a bolus.

13. The feed composition or feed additive of claim 9, wherein the antibiotic is at least one selected from the group consisting of monensin, lasalocid, narasin, maduramycin, semduramycin, salinomycin, avoparcin, actaplanin, and penicillin.

14. The feed composition or feed additive of claim 9, which further comprises at least one additional active substance selected from the group consisting of diallyl disulfide, garlic oil, allyl isothiocyanate, deoxycholic acid, chenodeoxycholic acid and derivatives thereof.

15. The feed composition or feed additive of claim 9, wherein the ruminant animal is selected from the group consisting of cattle, goats, sheep, giraffes, American Bison, European bison, yaks, water buffalo, deer, camels, alpacas, llamas, wildebeest, antelope, pronghorn, and nilgai.

* * * * *